United States Patent [19]

Ford

[11] Patent Number: 5,879,634
[45] Date of Patent: Mar. 9, 1999

[54] HIGH PRESSURE CONTAINMENT ASSEMBLY

[75] Inventor: Gordon C. Ford, St. Joseph, Mich.

[73] Assignee: Leco Corporation, St. Joseph, Mich.

[21] Appl. No.: 801,586

[22] Filed: Feb. 28, 1997

Related U.S. Application Data

[60] Provisional application No. 60/011,915 Feb. 20, 1996.
[51] Int. Cl.$^6$ .............................. B01D 11/00; B65D 51/16
[52] U.S. Cl. .............................. 422/102; 422/63; 422/70; 422/81; 422/101; 436/177; 436/178; 220/801; 220/804; 210/446; 210/450; 210/634
[58] Field of Search ................................ 422/63, 81, 101, 422/102, 103, 104; 436/43, 174, 175, 177, 178, 180; 210/511, 634, 446, 450; 220/203.09, 203.01, 234, 240, 801, 804

[56] References Cited

U.S. PATENT DOCUMENTS

| | | | |
|---|---|---|---|
| 5,173,188 | 12/1992 | Winter et al. | 210/634 |
| 5,179,551 | 1/1993 | Averette | 210/640 |
| 5,193,703 | 3/1993 | Staats, III et al. | 220/203 |
| 5,296,145 | 3/1994 | Allington et al. | 210/541 |
| 5,578,201 | 11/1996 | Collier et al. | 210/142 |
| 5,637,209 | 6/1997 | Wright et al. | 210/137 |
| 5,647,976 | 7/1997 | Rothe et al. | 210/137 |
| 5,660,727 | 8/1997 | Gleave et al. | 210/141 |
| 5,670,048 | 9/1997 | Davison et al. | 210/634 |

OTHER PUBLICATIONS

*Supercritical Fluid Extraction,* C&EN, Mar. 22, 1993.
*Supercritical Fluid Chromotography and Extraction,* C&EN, Mar. 23, 1993.
*Supercritical Fluid Extraction* brochure from ISCO, Inc., Mar., 1993.
ISCO, Inc. Price List, Feb. 22, 1993.
*Discover a More Cost–Effective Way to Prepare Samples* brochure from Hewlett Packard, 1992.
*Finally, True SFE Automation Has Arrived from the Leader in SF Technology* Brochure by Suprex Corporation, Published more than one year ago.
*Supercritical Fluid Extraction* brochure by Suprex Corporation Published more than one year ago.
*SFE–703 Supercritical Fluid Extraction System* brochure by Dionex, Lee Scientific Division, 1992.
*Series SF3™, Supercritical Fluid Chromatography with Packed Columns* brochure by Gilson Medical Electronics, Inc., Feb. 1, 1993.
B. S. Musser et al., *New Innovations in High Pressure Supercritical Fluid Extraction Vessels,* Keystone Scientific, Inc., 1993.
*Microwave Moisture and Fat Analysis System* brochure by CEM Corporation, Published more than one year ago.
Advertisement by Tecator, A Perstorp Analytical Company, published more than one year ago.
Antonacci, et al., *Improved Product Quality and Improved Cost Formulations,* Meat Industry—Published by Tecator, Feb. 1993.
Tehrani, Joe, *Successful Supercritical Fluid Extraction Strategies,* published more than one year ago.

(List continued on next page.)

*Primary Examiner*—Long V. Le
*Attorney, Agent, or Firm*—Price, Heneveld, Cooper, DeWitt & Litton

[57] ABSTRACT

An assembly for extracting analytes from a sample using a fluid under pressure, and embodying the invention, includes an extraction cell receiving the sample and having a chamber body closed at one end by a translatable slide block assembly in fluid communication with the fluid under pressure to introduce the fluid under pressure into the sample located within the chamber body; and a cylinder block assembly at the opposite end of the chamber body for extracting the fluid passing through the sample, the sample being enclosed in a vessel having a thimble body closed at opposite ends by pressure-fit end cap assemblies, each having a thimble cap, a seal, and a frit cap assembly for retaining the sample within the thimble body and permitting the passage of the fluid therethrough.

10 Claims, 6 Drawing Sheets

OTHER PUBLICATIONS

Levy, J. et al., *Developments in Off–Line Collection for Supercritical Fluid Extraction,* Apr. 1993.

Mulcahey, L.J. et al., *Collection Efficiency of Solid Surface and Sorbent Traps in Supercritical Fluid Extraction with Modified Carbon Dioxide,* American Chemical Society, 1992.

Wallace, J. et al., *Reduction of Contamination Levels in On–Line Supercritical Fluid Extraction Systems,* Analytical Chem., 1992, 64, 2655–2656.

Thomson, C.A. et al., *Supercritical Carbon Dioxide Extraction of 2,4–Dichlorophenol from Food Crop Tissues,* Anal. Chem., 1992, 64, 848–853.

*Supercritical Fluid Technology,* U.S. Department of Agriculture, published more than one year ago.

*Cutting Use of Laboratory Solvents,* Agricultural Research, Mar. 1993.

King, J.W., *Analytical Supercritical Fluid Extraction: Current Trends and Fiture Vistas,* Journal of AOAC Inter'l, vol. 75, No. 3, 1992.

King, J.W. et al., *Translation and Optimization of Supercritical Fluid Extraction Methods to Commercial Instrumentation,* Journal of Chromatographic Science, vol. 31, Jan. 1993.

France, J.E. et al., *Supercritical Fluid–Based Cleanup Technique for the Separation of Organochlorine Pesticides n from Fats,* Journal of Agricultural & Food Chemistry, Oct. 1991.

King, J.W. et al., *Extraction of Fat Tissue from Meat Products with Supercritical Carbon Dioxide,* Agricultural & Food Chemistry, Jul./Aug. 1989, American Chemical Society.

Untitled articles from Research & Development, Mar. 1991.

King, J.W. et al., *Basic Principles of Analytical Supercritical Fluid Extraction,* Springer–Verlag Berlin Heidelberg, 1992.

France, J.E. et al., *Supercritical Fluid–Based Cleanup Technique for the Separation of Organochlorine Pesticides n from Fats,* Journal of Agricultural & Food Chemistry, Oct. 1991. Undated article entitled *Better Meat Products,* published more than one year ago.

Undated article entitled *Better Meat Products,* published more than one year ago.

Squires, T.G. et al., *Supercritical Fluids Chemical and Engineering Principles and Applications,* ACS Symposium Series, Sep. 1985.

Supercritical Fluid Technologies, Inc. brochure, 1996.

Supercritical Fluid Extraction from ISCO brochure dated Feb. 1996.

Supercritical Fluid Extraction brochure from Dionex dated Jan. 1993.

Westwood, S.A., *Supercritical Fluid Extraction and Its Use in Chromatographic Sample Preparation,* Blackie Academic & Professional, published more than one year ago.

Taylor, S.L. et al., *Determination of Oil Content in Oilseeds by Analytical Supercritical Fluid Extraction,* American, JAOCS, vol. 70, No. 4, Apr. 1993.

Kirschner, C.A. et al., *Quantitative Analysis by On–Line Supercritical Fluid Extraction/Fourier Transform Infrared Spectrometry,* Anal. Chem., 65, 78–83, 1993.

HIGH PRESSURE CONTAINMENT ASSEMBLY

CROSS-REFERENCE TO RELATED APPLICATION

This application claims the benefit of U.S. Provisional Application No. 60/011,915, filed Feb. 20, 1996.

BACKGROUND OF THE INVENTION

1. Field of the Invention

This concept relates to containment vessels in general and, particularly, to a sample containment vessel assembly for extracting fats from samples using supercritical fluid extraction techniques.

2. Discussion of the Related Art

It has become important to be able to determine the amount and type of fat within a product. Devices for extracting and measuring the fat content of products have been around for some time. One type of system utilizes pressurized fluid as a solvent to remove fats or other constituents from the sample. This process, generally known as supercritical fluid extraction, requires that the fluid pass through the sample under pressure in order to mobilize the constituent of interest. The pressures required to carry out the process may be on the order of thousands of pounds per square inch. Containment vessels for retaining the sample were required which would not rupture under such pressures. The containment vessels typically consisted of a steel housing threaded at each end and sealed by large, bulky threaded plugs. The plugs were then attached by threaded fittings to the pressure source and the sample receiving container.

The disadvantage with the prior systems is that the operator needed to connect and disconnect the fittings and the plugs before and after each sampling. This increased the sampling time, and as a direct result, the overall cost of conducting the procedure. Furthermore, the containment vessels were often very large in order to contain the sample under pressure. The concept disclosed and claimed herein provides rapid sample loading and unloading, and automatically seals the sample within a much smaller containment vessel than previously achieved, resulting in increased production and reduced cost.

SUMMARY OF THE INVENTION

In general, an assembly for extracting analytes from a sample includes a vessel for retaining the sample and configured to allow fluid to pass through the sample, a chamber assembly for receiving and substantially surrounding the vessel; a slide block assembly mounted to one end of the chamber assembly having a conduit therein in fluid communication with the vessel to introduce the fluid into the vessel at pressure to mobilize any analytes within the sample; and a cylinder block assembly at an opposite end of the chamber assembly and having a conduit in fluid communication with the opposite end of the vessel for extracting the fluid therefrom, along with any analytes mobilized by the fluid.

In another form of the assembly embodying the invention, the chamber assembly includes at least one chamber configured to receive a vessel in a direction generally coincidental with the longitudinal axis of the vessel. A chamber assembly which defines the chamber includes at least one actuator for moving the vessel with respect to the chamber assembly. A slide block assembly located at one end of the chamber assembly includes at least one transverse hole extending therethrough for permitting passage of the vessel into the chamber assembly; a conduit within the slide block assembly terminates in at least one discharge port located on the first side of the slide block facing the chamber assembly and adjacent each transverse hole with at least one inlet port on another side of the slide block. The vessel includes a tubular body open at opposite ends so the sample may be located therein, and the tubular body is closed at each end by a press-fit cap assembly, each having a passage for permitting the fluid to pass therethrough.

Another form of the device for extracting analytes and embodying the invention includes a vessel having a tubular housing open at opposite ends for retaining the sample under pressure; an end cap assembly is disposed in each end of the vessel to close the vessel and help retain the sample therein, each end cap assembly having a cap with an axial bore with one end received in the vessel, a frit disposed at the end of the cap within the vessel, and a gasket assembly located intermediate the frit and the opposite end of the cap for sealing the end cap assembly within the vessel. The concept embodying the invention also includes a chamber assembly for receiving the vessel therein; a slide block assembly slidably disposed over one end of the chamber assembly to retain the vessel therein, and having a conduit in fluid communication with the vessel through one of the end cap assemblies for introducing a fluid into the sample under pressure; and a cylinder block assembly closing an opposite end of the chamber assembly and having a conduit in fluid communication with an opposite end of the vessel through an opposite end cap assembly to extract the fluid passing through the sample. As further defined, the end cap assembly includes a frit holder slidably received within the axial bore of the cap and having a passage extending therethrough concentric with the axial bore, a flange at a first end of the cap for holding the frit over the passage; and a means for retaining the frit holder against the first end of the cap.

In yet another form of the invention, an assembly for extracting analytes from a sample using a fluid under pressure and embodying the invention includes an extraction cell receiving the sample and having a chamber body closed at one end by a translatable slide block assembly in fluid communication with the fluid under pressure to introduce the fluid under pressure into the sample located within the chamber body, and a cylinder block assembly at the opposite end of the chamber body for extracting the fluid passing through the sample, the sample being enclosed in a vessel having a thimble body closed at opposite ends by pressure fit end cap assemblies, each having a thimble cap, a seal, and a frit cap assembly for retaining the sample within the thimble body and permitting the passage of the fluid therethrough.

The advantages provided by this system include a more expeditious loading and unloading of samples due to the abolition of threaded couplings. Moreover, when the sample is loaded within the vessel and placed within the extraction assembly, the sample is automatically sealed within the vessel. The improvements of this invention include increased productivity and fewer man hours than achievable using conventional systems. Furthermore, it is believed that the assembly embodying this invention is less expensive to build as a result of fewer materials and machining.

These advantages, and others, will be realized after a review of the drawing figures and detailed description provided below.

BRIEF DESCRIPTION OF THE DRAWING FIGURES

FIG. 1 generally illustrates one example of a device embodying the concept described herein;

DETAILED DESCRIPTION OF THE PREFERRED EMBODIMENT

Figure 1:
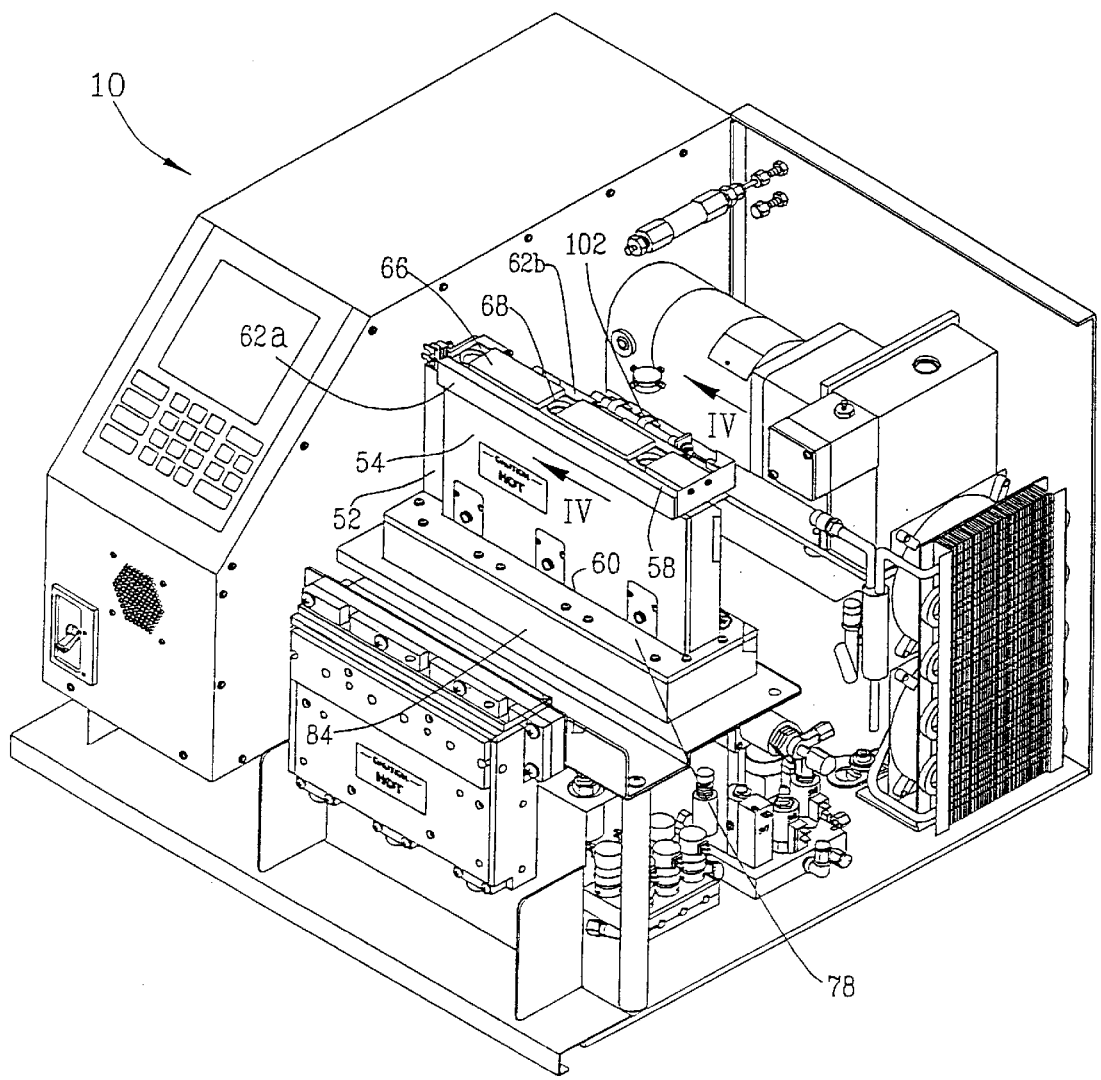

FIG. 1 generally illustrates one version of a fat analyzer 10 available from Leco Corporation of St. Joseph, Mich., under the brand FA-100®. Instrument 10 is a microprocessor based design for extracting analytes from samples using the supercritical fluid extraction technique mentioned above. The automated system, operated under the control of a microprocessor, provides the ability to extract analytes from multiple samples at the same time. Once a sample has been processed and allowed to return to atmospheric pressure, the sample container is raised and removed by the operator where more samples can be quickly reloaded. Under the direction of the microprocessor, one or more samples are automatically located in the pressure chamber and sealed, placed under pressure, saturated with supercritical fluid to extract the analyte, and allowed to return to atmospheric pressure. The procedure is then repeated.

Figure 2:
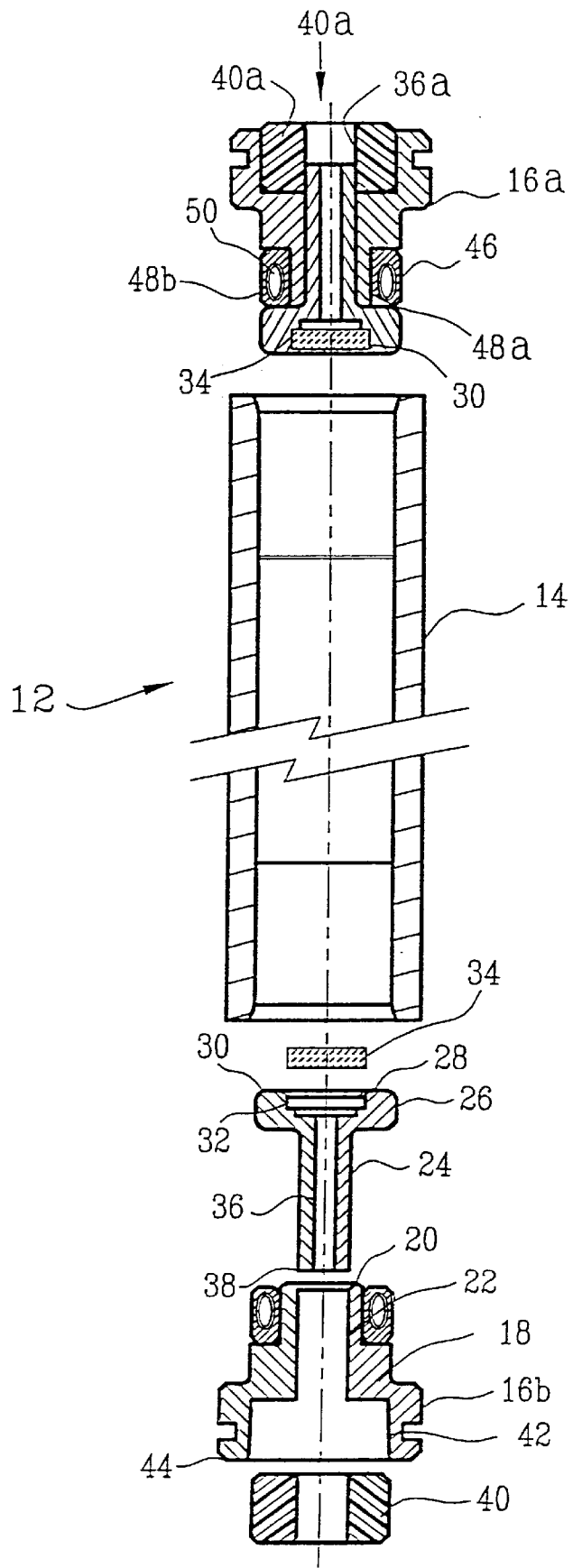
FIG. 2 is an elevation section view of a sample containment vessel comprising part of this concept.
Figure 3:
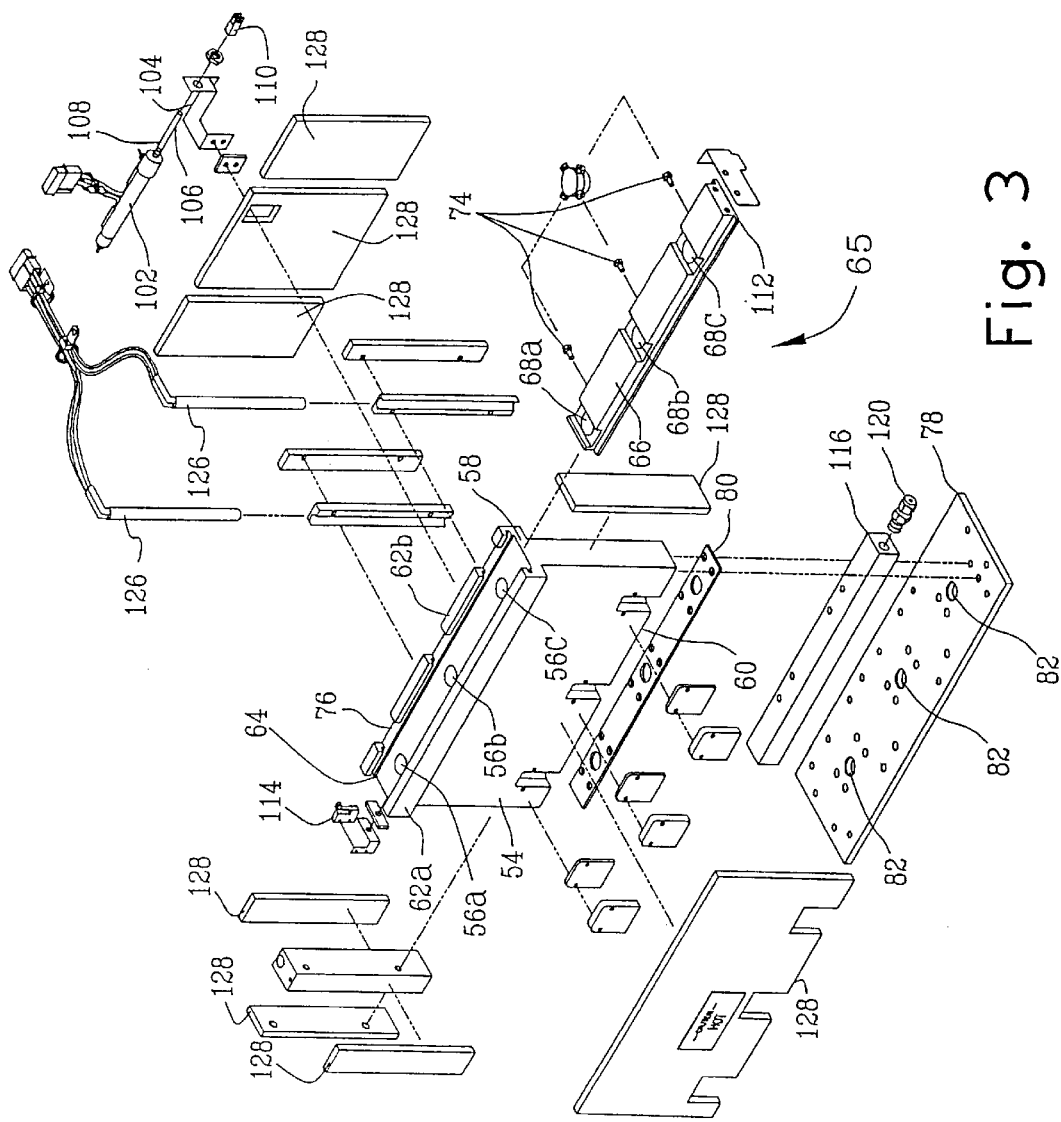
FIG. 3 is an exploded view of an upper portion of a chamber assembly and slide block assembly comprising a part of the concept.
Figure 4:
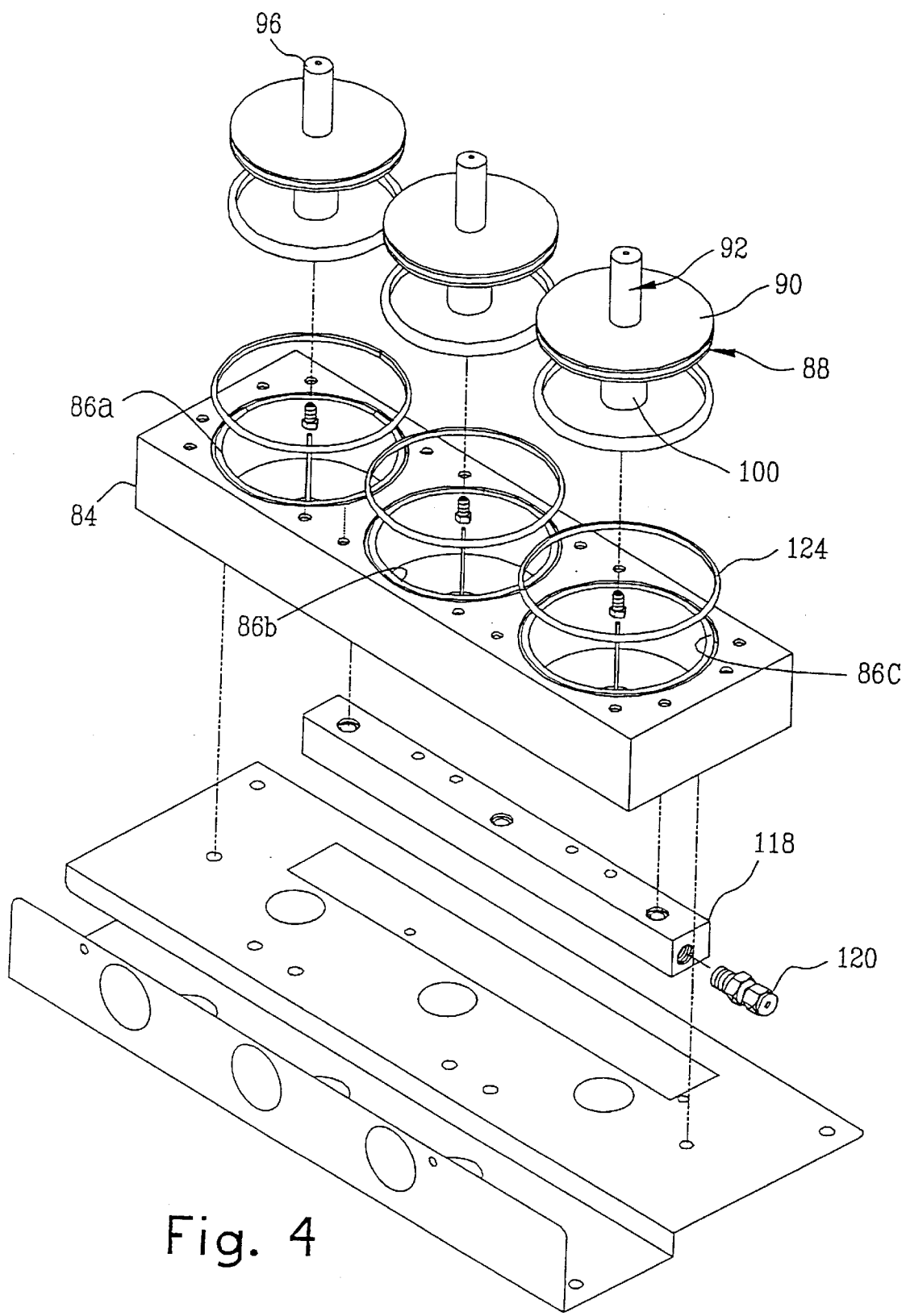
FIG. 4 is an exploded view of a cylinder block assembly comprising a part of the concept.

The components primarily responsible for receiving and sealing the sample within analyzer 10 are shown in FIGS. 2–4. FIG. 2 is an elevation section view of one embodiment of a sample containment vessel 12 embodying the concept. The sample containment vessel or "thimble" assembly 12 includes a tubular body 14, preferably made from stainless steel or other high-strength material, and is open at opposite ends. The ends of the body receive thimble cap assemblies 16a, 16b, each slidably received in the ends of body 14. Each thimble cap assembly 16 includes a cap 18 having one end 20 dimensioned to be received within the end of the thimble body. The cap also includes an axial bore 22 extending therethrough which receives a shaft 24 of a frit holder 26. One end 28 of the frit holder terminates in a cylindrical flange or button. The face 30 of flange 28 contains a depression or recess 32 configured to receive a porous and permeable disk or frit 34 therein. Depression 32 is in fluid communication through an axial bore 36 extending through the shaft to the opposite end of thimble cap 18. The end of shaft 38 opposite flange 28 is preferably threaded and retained in cap 18 by a retainer 40. The thread hole 36a in nut 40, which receives shaft 38, constitutes an extension of bore 36 to define a port 40a at each end of the thimble. In a preferred embodiment, cap 18 and frit holder 26 are made from stainless steel, frit 34 is made from sintered stainless steel or other corrosion-free, permeable material, and retainer or nut 40 is made from polyethylene ethylketone (PEEK) or having the desired characteristics of polymeric material. It is further preferred that retainer 40 be received within depression 42 defined in end 44 of cap 18. The inner end 20 of cap 18 is dimensioned to receive a seal 46. Further, seal 46 is presented to make a seal between end cap 18 and the inner wall of thimble body 14. Seal 46 is preferably an O-ring or radial seal having inner and outer walls 48a, 48b separated by a spring 50. It is also preferred that the opening between inner and outer walls 48a, 48b and retaining the spring be oriented inwardly toward thimble body 14.

In operation, one end of the thimble body is closed by one of the thimble cap assemblies. The sample to be analyzed is loaded into the thimble body through the opposite open end. Once the desired amount of sample has been placed therein, the thimble body is closed by the remaining thimble cap assembly. The dimensions of the ends of the thimble caps and the frit holder flange are such that the thimble cap assemblies can be inserted and removed by hand. However, it is preferred that close tolerances be adhered to as much as possible in order to ensure that radial seal 46 is not extruded through the space between the thimble body and thimble cap, known as the E-gap. Furthermore, gasket 46 is preferably made from a material which resists extrusion through the E-gap, even at pressures on the order of 12,000 pounds per square inch (psi).

Referring to FIG. 3, one or more thimble assemblies 12, such as described above, are received in a chamber assembly 52. Chamber assembly 52 includes a chamber body 54 preferably machined from bar stock aluminum. In the preferred configuration, chamber body 54 contains several spaced holes or chambers 56a, 56b, and 56c each parallel to the other and all extending from upper edge 58 to lower edge 60. Flanges 62a, 62b are machined along upper edge 58 to provide channels or tracks 64 which parallel the upper edge. A slide block assembly 65 includes a slide block 66 received in channels 64 to slide along upper edge 58 of chamber block 54. Holes 68a, 68b, and 68c are provided through slide block 66 in a manner to align with chambers or bores 56a, 56b, 56c in chamber block 54. Adjacent each hole 68a–68c and defined on the lower surface 70 of slide block 66 is an orifice 72 (FIGS. 5, 6), each configured to align with one of bores 56a–56c in chamber block 54 and bore 36 in cap assembly 18 when slide block 66 translates within channels 64. Each orifice or port 72 is connected through a series of passages to fittings 74 received in ports 75 defined along edge 75a. Spaces 76 in one of flanges 62b accommodates for the translational movement of the fittings extending from slide block 66.

Figure 5:
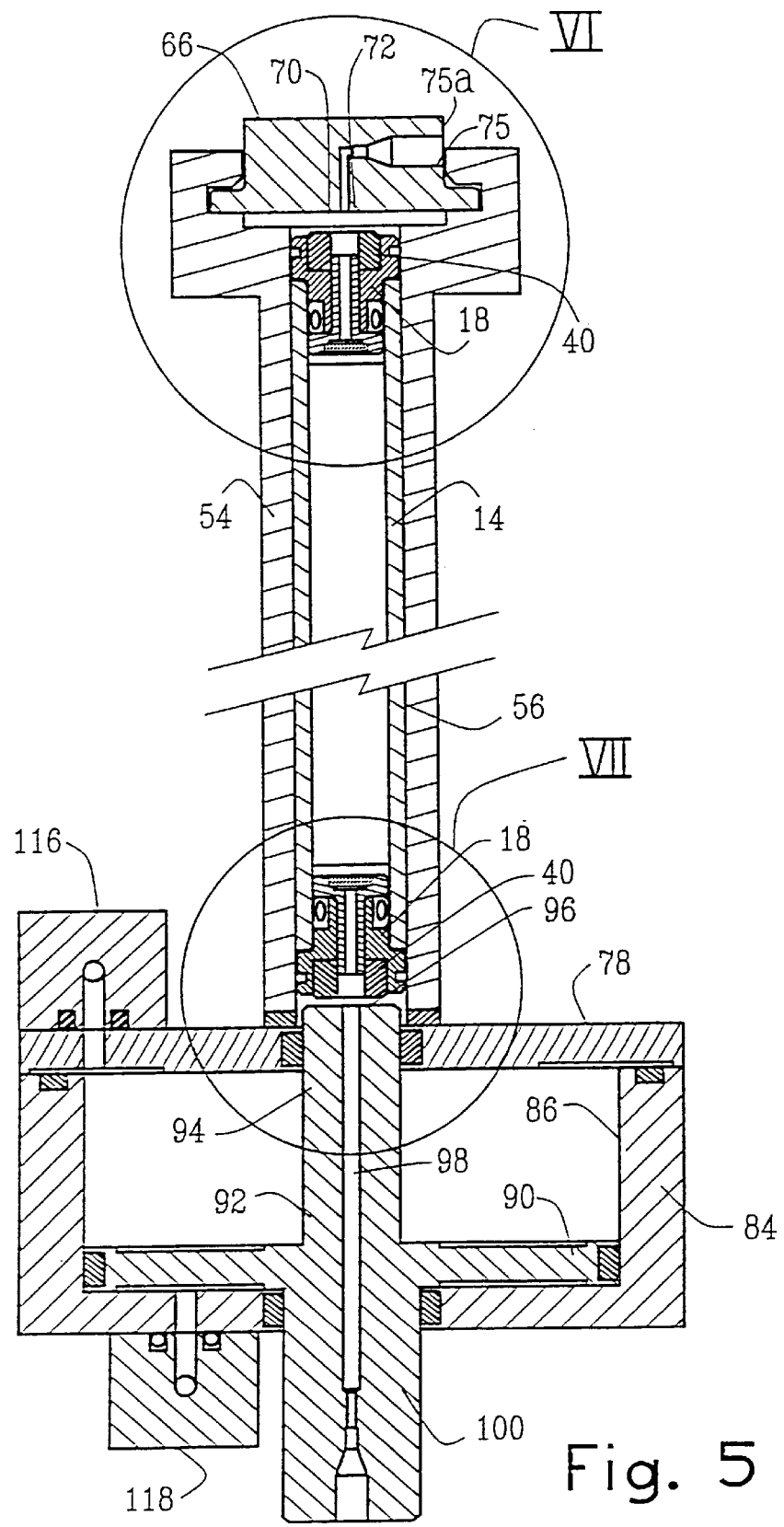
FIG. 5 is an elevation view in section of the chamber assembly, slide bock assembly, and cylinder block assembly.
Figure 7:
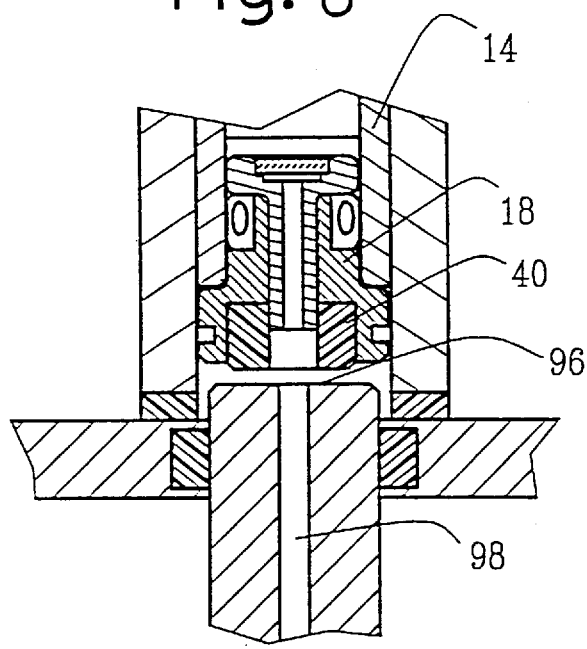
FIG. 7 is a detailed view of the lower portion of the chamber and the cylinder block assembly illustrated within detail VII shown in FIG. 5.

At the lower end 60 of chamber body 54 is a cover plate 78, separated from chamber body 54 by a gasket spacer 80 (FIG. 3). Extending through spacer 80 and cover 78 in alignment with each chamber bore 56a–56c is a hole 82. Cover plate 78 is, in turn, attached to the top of a cylinder block 84 (FIG. 4) containing a number of cylinder bores 86a, 86b, 86c equal to the number of chamber bores 56a–56c. Disposed in each cylinder bore 86a–86c is an actuator 88 having a piston 90 centrally disposed on a tubular piston shaft 92. An upper end 94 of each piston shaft 92 extends through the respective openings 82 in cover plate 78 and spacer 80 and into the lower end 60 of a respective chamber bore 56a–56c. Upper end 94 of each piston shaft 92 contains a flat 96 configured to compress against retainer 40 on the lower end of thimble assembly 12 (FIGS. 5, 7). Flat 96 is specifically configured to seal with opening 36a of retainer 40. A passage 98 is provided through each piston shaft 92 and out the lower end 100, which is in fluid communication with a valve assembly (not shown). Below the valve assembly, outlets are provided for each passage, below which are located containers for receiving the analyte extracted from the samples. The containers may, in turn, be resting on a scale wherein the tare weight and sample weight of the containers may be quickly measured.

Actuation of slide block 66 and pistons 90 are preferably fluid controlled, such as air or a liquid. In one embodiment, a linear actuator 102 (FIGS. 1, 3) is mounted by a bracket 104 or similar structure proximate upper edge 58 of chamber body 54. A free end 106 of the actuator ram or shaft 108 is coupled to one end 112 of slide block 66, preferably via a clevis 110 or other flexible connector. Thus, translation of actuator 102 results in translation of slide block 66 over chamber bores 56a–56c. A switch 114 may be provided, either on actuator 102 or on one end of chamber body channel 64 near one end of slide block 66, to determine when the slide block is in the closed position. With respect to pistons 90 (FIGS. 3–5), manifolds 116, 118 may be located on the upper and lower covers, respectively, each connected via a fitting 120 and tube (not shown) to a source of pressurized fluid, i.e., nitrogen or the like. By actuating a valve interconnecting the two manifolds, gas is introduced to one side or the other of pistons 90. In one embodiment, pistons 90 should be able to exert at least 1,000 pounds of force at flat 96, engaging the lower thimble cap, preferably about 1,500 pounds of force, and most preferably at least 1,600 pounds of force. It is contemplated that conventional O-ring seals 124 can be used about the periphery of the pistons and around each cylinder at the junction with the cover plates. For safety, a pop-off valve is located either in manifolds 116, 118 or in the lines coupled to fittings 120. The pop-off valve (not shown) is intended to prevent overpressurization of chamber 86 on either side of piston 90. The pop-off pressure should be greater than the normal operating pressure.

Chamber assembly 52 may also include one or more heating elements 126a, 126b configured to heat chamber body 54. Elements 126a, 126b may be mounted to the exterior of chamber body 54, or mounted within a recess (not shown) formed in the chamber body. In a preferred embodiment, heating elements 126a, 126b are capable of heating chamber body 54 to a temperature of greater than 100° C. To maintain the temperature of the chamber body and to prevent excessive heating of the other components within the instrument cabinet, chamber body 54 is substantially surrounded with insulative sheeting, such as 128, and controlled by a thermocouple (not shown).

Figure 6:
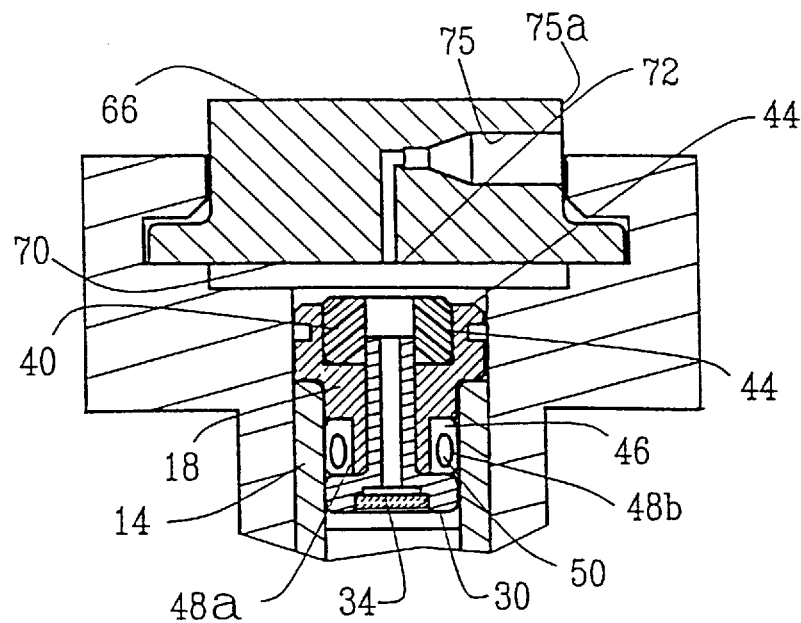
FIG. 6 is a detailed view of the upper portion of the chamber and slide block assembly illustrated within detail VI shown in FIG. 5.

Referring to FIGS. 3, 5, and 6, initially the slide block is in the open position, translated to align openings 68a–68c therein with the chamber bores 56a–56c. The extraction system may already have run through any self-diagnostic testing and preheated the chamber body if necessary for the particular procedure. One or more thimble assemblies 12 containing a sample as described above are loaded through holes 68a–68c in slide block 66 into respective bore 56a–56c in chamber body 54. At this initial stage of the process, and after the slide block has opened fully, piston shafts 92 are actuated upwardly into chamber body 54 such that each of the thimble assemblies 12 is elevated slightly above the upper edge of slide block 66. With the thimble assemblies loaded, and upon a signal from the operator, the microprocessor-controlled system lowers each of the pistons, lowering the thimble assemblies 12 into bores 56a–56c of chamber body 54. Once lowered, slide block 66 is translated to cover each of the bores 56a–56c. When fully closed, slide block 66 engages switch 114, indicating that block 66 is fully closed and ready for pressurization. At this point, piston shafts 92 are actuated upwardly so that flats 96 on ends 94 engage and seal with port 36a in retainer 40. Additionally, each thimble assembly 12 is forced upward in each bore 56a–56c until orifices 72 on lower surface 70 of block 66 engage and seal against port 40a in the end of upper retainer 40. At this point, the appropriate valves are actuated to begin pressurizing the thimble assemblies. At the appropriate pressure—approximately 9,000 psi—the appropriate gas or fluid is introduced through slide block 66, through the interior of thimble assembly 12, and out through tubular piston shafts 92 wherein the analyte removed from the enclosed sample is deposited in the container. Once the desired assay has been completed, depressurization of the thimbles occurs. Once at ambient pressure, pistons 90 are lowered to allow thimble assembly 12 to disengage orifices 70. Slide block 66 is opened, and pistons 90 extend to move thimble assemblies 12 up and out of bores 56a–56c. The operator then removes thimble assemblies 12 from the instrument and repeats the steps.

It is contemplated that a system may be included to prevent pressurization of the sample containment vessel 46 if there is not sufficient pressure to seal vessels 40 within chamber assembly 42. For example, a sensor (not shown) could be operably coupled to manifold 118 to detect the fluid pressure in the high-pressure side of the system. A threshold pressure would need to be satisfied and conveyed to the central processor prior to activation of the fluid extraction system and pressurization of sample containment vessels 40. Without such a safety it is possible that the sealing pressure would not off-set the pressure within the containment vessel, resulting in separation of the seals at one or both ends of vessels 40 and venting of the analyte and carrier solvents.

It is contemplated that this concept certainly has applications outside supercritical fluid extraction instruments. Any instrument or method requiring the use of pressurized vessels can benefit from this concept. This concept removes the need to use outmoded, threaded coupling to achieve a tight seal with a containment vessel. Although the above description is made with specific reference to supercritical fluid applications, this system can be used elsewhere and is contemplated to be within the teachings and scope of this concept.

I claim:

1. An assembly for extracting analytes from a sample under pressure, comprising in combination:

a vessel having a tubular housing, open at opposite ends, for retaining the sample under pressure; and an end cap assembly slidably received in an axial direction in each end of said vessel to close said vessel and help retain the sample therein, each end cap assembly including a cap having an axial bore extending therethrough with a first end received within said vessel, a frit disposed at said first end of said cap over said axial bore, and a gasket assembly intermediate said frit and an opposite end of said cap for sealing said end cap assembly within said vessel.

2. The assembly as defined in claim 1, further including:

a chamber assembly for receiving said vessel therein;

a slide block assembly, slidably disposed over one end of said chamber assembly to retain said vessel therein, and having a conduit therein in fluid communication with said vessel through one of said end cap assemblies for introducing a fluid into the sample under pressure; and a cylinder block assembly closing an opposite end of said chamber assembly and having a conduit therein in fluid communication with an opposite end of said vessel through an opposite end cap assembly for extracting the fluid passing through the sample.

3. The assembly as defined in claim 1, wherein said end cap assembly further includes:

a frit holder slidably received within said axial bore of said cap and having a passage extending therethrough concentric with said axial bore, and a flange at a first end for holding said frit therein over said passage; and a means for retaining said frit holder against said first end of said cap.

4. The assembly as defined in claim 2, further including a heater assembly located with respect to said chamber assembly for heating the sample within said vessel to aid in the mobilization and extraction of the analytes within the sample.

5. The assembly as defined in claim 2, further including a linear actuator interconnecting said chamber assembly and said slide block assembly for translating said slide block assembly over said one end of said chamber assembly.

6. The assembly as defined in claim 2, wherein said chamber assembly includes a chamber body having at least one cylindrical chamber extending therethrough from a first end to a second end, and said first end having a transverse channel defined therein for receiving said slide block assembly in sliding arrangement over said first end.

7. The assembly as defined in claim 2, wherein said cylinder block assembly includes an actuator assembly for moving said vessel with respect to said chamber assembly, said conduit within said cylinder block assembly extending through said at least one actuator.

8. The assembly as defined in claim 4, wherein said heater assembly includes at least one heating element attached to an exterior of said chamber assembly.

9. The assembly as defined in claim 4, wherein said heater assembly includes at least one heating element disposed within said chamber assembly.

10. The assembly as defined in claim 7, wherein said actuator includes:

a piston shaft having a first end disposed in said chamber assembly and a second end extending from said cylinder block assembly, said conduit in said cylinder block assembly extending through said piston shaft; and a piston disposed on said piston shaft intermediate said first and second ends.

* * * * *